United States Patent
Behfar et al.

(10) Patent No.: US 10,596,123 B2
(45) Date of Patent: Mar. 24, 2020

(54) EXOSOME DELIVERY TECHNOLOGY

(71) Applicant: Mayo Foundation for Medical Education and Research, Rochester, MN (US)

(72) Inventors: Atta Behfar, Rochester, MN (US); Andre Terzic, Rochester, MN (US); William Cook, Rochester, MN (US); Ruben Crespo, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/067,799

(22) Filed: Mar. 11, 2016

(65) Prior Publication Data

US 2016/0324794 A1 Nov. 10, 2016

Related U.S. Application Data

(60) Provisional application No. 62/131,504, filed on Mar. 11, 2015.

(51) Int. Cl.
| | |
|---|---|
| *A61K 9/50* | (2006.01) |
| *A61K 8/11* | (2006.01) |
| *A61K 8/14* | (2006.01) |
| *A61K 8/98* | (2006.01) |
| *A61K 35/16* | (2015.01) |
| *A61Q 19/00* | (2006.01) |

(52) U.S. Cl.
CPC .............. *A61K 9/5089* (2013.01); *A61K 8/11* (2013.01); *A61K 8/14* (2013.01); *A61K 8/983* (2013.01); *A61K 9/5073* (2013.01); *A61K 35/16* (2013.01); *A61Q 19/00* (2013.01); *A61K 2800/10* (2013.01); *A61K 2800/412* (2013.01)

(58) Field of Classification Search
CPC ........ A61K 8/14; A61K 8/983; A61K 9/5073; A61K 9/5089; A61K 35/16; A61K 9/1617; A61K 9/1652; A61K 9/1694; A61K 8/11; A61K 2800/10; A61K 2800/412; A61Q 19/00
See application file for complete search history.

(56) References Cited

U.S. PATENT DOCUMENTS

| | | | |
|---|---|---|---|
| 6,235,274 B1 | 5/2001 | Lou et al. | |
| 6,413,548 B1 | 7/2002 | Hamer et al. | |
| 8,183,118 B2 | 5/2012 | Lu et al. | |
| 8,835,384 B2 | 9/2014 | Terzic et al. | |
| 2004/0175328 A1 | 9/2004 | Sutton et al. | |
| 2006/0051425 A1 | 3/2006 | Kvitnitsky et al. | |
| 2008/0019944 A1 | 1/2008 | Terzic et al. | |
| 2008/0213214 A1 | 9/2008 | Terzic et al. | |
| 2010/0189697 A1 | 7/2010 | Terzic et al. | |
| 2011/0014251 A1 | 1/2011 | Ray | |
| 2011/0014261 A1 | 1/2011 | Ray | |
| 2011/0117065 A1 | 5/2011 | Terzic et al. | |
| 2012/0178164 A1 | 7/2012 | Terzic et al. | |
| 2012/0308650 A1 | 12/2012 | Vegas et al. | |
| 2012/0315324 A1* | 12/2012 | Zhang | A61K 31/05 424/450 |

FOREIGN PATENT DOCUMENTS

| | | |
|---|---|---|
| WO | WO 2012/053976 A1 | 4/2012 |
| WO | WO 2014/159662 A1 | 10/2014 |

OTHER PUBLICATIONS

Muller et al. Isolation of biologically-active exosomes from human plasma. Journal of Immunological Methods (2014), v411, p. 55-65. (Year: 2014).*
Turchinovich et al. Characterization of extracellular circulating microRNA. Nucleic Acids Research (2011), v39(16), p. 7223-7233. (Year: 2011).*
Logozzi et al. High Levels of Exosomes Expressing CD63 and Caveolin-1 in Plasma of Melanoma Patients. PLoS One (2009), v4(4), e5219, 10 pages. (Year: 2009).*
Lamparski et al. Production and characterization of clinical grade exosomes derived from dendritic cells. Journal of Immunological Methods (2002), v270, p. 211-226; (Year: 2002).*
International Search Report and Written Opinion, International Patent Application No. PCT/US2016/022050, dated Jun. 7, 2016, 12 pages.
International Preliminary Report on Patentability, International Patent Application No. PCT/US2016/022050, dated Sep. 21, 2017, 12 pages.
Qinyu et al., "miRNA in Plasma Exosome is Stable under Different Storage Conditions," *Molecules*, 2014; 19:1568-1575.
European Patent Application No. 16762612.6, filed Oct. 10, 2017, Supplementary European Search Report dated Oct. 12, 2018.

* cited by examiner

*Primary Examiner* — Sean C. Barron
(74) *Attorney, Agent, or Firm* — Mueting, Raasch & Gebhardt, P.A.

(57) ABSTRACT

A method of delivering exosomes and other micro vesicles to a biological target includes the steps of 1) providing blood, (2) separating plasma from the provided blood, and (3) separating the solution with the exosomes therefrom, (4) encapsulating the exosomes, and (5) delivering the exosomes. The step of encapsulation may be accomplished by water bead process, alginate bead process, spray drying bead formation, or plating. The biological target may be a human or animal heart, bone/joint, wound or skin. A method of encapsulating an exosome, a method of using an encapsulated exosome, compositions including encapsulated exosomes, and an encapsulated exosome per se are also disclosed.

27 Claims, 7 Drawing Sheets

EXOSOME DELIVERY TECHNOLOGY

CROSS REFERENCE TO RELATED APPLICATIONS, IF ANY

This application claims the benefit under 35 U.S.C. § 119(e) of co-pending U.S. Provisional Patent Application Ser. No. 62/131,504, filed Mar. 11, 2015, which is hereby incorporated by reference.

37 C.F.R. § 1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

Field of the Invention

The present invention relates, generally, to biotechnology systems, apparatus, compositions and methods. Particularly, the invention relates to human regenerative medicine and therapies used in cardiology, dermatology, orthopedics, surgery, wound care, and all restorative healthcare applications. Most particularly, the invention relates to encapsulated exosomes, apparatus for encapsulating exosomes, methods for encapsulating exosomes, and methods for using encapsulated exosomes in the fields mentioned above. The systems, apparatus, compositions and methods of the invention are believed to be useful in other fields including but not limited to veterinary medicine and cosmetic compositions and methods.

Background Information

Regenerative medicine therapies and methods hold great promise for treating disease and other conditions in the fields of cardiology, dermatology, orthopedics, surgery, wound care, and other medical and surgical fields. These methods utilize materials from various human and other animal cells, including blood and other stem cells. Exosomes are small vesicles (small structures within a cell consisting of fluid enclosed by a lipid bilayer membrane) that are present in many biological fluids, including blood. (See FIG. 1) Exosomes typically have a diameter between 30 and 100 nm. They contain Ribonucleic acid (RNA), proteins, lipids and various metabolites. Exosomes appear to play a role m coagulation, cellular signaling, and waste management. It has been believed that exosomes may potentially be used for medical prognosis, medical therapy, and as biomarkers.

Platelet exosomes are present when blood platelets (mammalian blood cells approximately 2-3 um in diameter) are physically disrupted by various means. Referring to FIG. 2, platelets are well known to function to stop bleeding (coagulation and hemostasis). However, platelets are believed to play a broad roll in healing of tissue in general as they increase tissue regeneration, collagen matrix formation, bone density, angiogenesis, pain relief, inflammation minimization, and overall healing in humans and other animals. The present, invention involves using encapsulated vesicles, encapsulated exosomes in particular, and encapsulated platelet exosomes most particularly, to regenerate, repair or restore damaged tissue and for other biological, medical, cosmetic, or hygienic purposes.

Existing technology in this field is believed to have significant limitations and shortcomings All US patents and patent applications, and all other published documents mentioned anywhere in this application are incorporated by reference in their entirety.

BRIEF SUMMARY OF THE INVENTION

The present Invention provides encapsulated exosomes or other small vesicles (hereinafter "vesicles" or "microvesicles"), encapsulation apparatus, methods of encapsulating exosomes and other vesicles, and methods for using encapsulated exosomes or other vesicles which are effective, safe, practical, reliable, and efficient, and which are believed to constitute an improvement over the background technology.

In a first aspect, the invention relates to a method of encapsulating exosomes or other vesicles including the steps of (1) collecting blood, (2) separating plasma from the collected blood, (3) separating a solution with the exosomes or other vesicles therefrom, and (4) encapsulating the exosomes or other vesicles.

In a second aspect, the blood that is collected in the first aspect is collected from humans.

In a third aspect, the blood that is collected in the first aspect is collected from the group of animals consisting of pigs, cows, sheep, and the like.

In a fourth aspect, the liquid volume of plasma collected from the blood in the first aspect is 0.5-50 percent, preferably 3-45 percent, and most preferably 10-40 percent.

In a fifth aspect, the step in the first aspect of separating a solution of exosomes or other vesicles from the separated plasma is accomplished via filtration or centrifugation.

In a sixth aspect, the step of filtration of the fifth aspect is accomplished with a 30-100 kDalton filter, preferably a 50-100 kDalton filter and most preferably a 50-80 kDalton filter, whereby material retained by the filter contains the desired exosomes.

In a seventh aspect, the liquid volume of exosomes extracted from the plasma in the first aspect is 0.5-40 percent, preferably 15-35 percent, and most preferably 20-30 percent.

In an eighth aspect, the exosome solution derived in the first aspect is preferably diluted 100 to 1.0 percent, preferably 25 to 2.5 percent and most preferably 15 to 5 percent.

In a ninth aspect, the step of encapsulating exosomes of the first aspect includes the steps of water bead delivery.

In a tenth aspect, the step of encapsulating exosomes of the first aspect includes the steps of alginate bead delivery.

In an eleventh aspect, the step of encapsulating exosomes of the first aspect Includes the steps of spray drying bead formation.

In a twelfth aspect, the step of encapsulating exosomes of the first aspect includes the steps of plating delivery.

In a thirteenth aspect, the first aspect Involves the further step of delivering the encapsulated exosomes to a biological target.

In a fourteenth aspect, the step of delivery in the thirteenth aspect involves delivery to a target selected from the group consisting of the heart, a bone or joint, a wound, and the skin, or other organs or tissues.

In a fifteenth aspect, the invention involves the steps of controlling the temperature at which the above-mentioned steps are accomplished and by limiting exposure to surfactants.

In a sixteenth aspect, the invention provides a therapy method comprising the steps of (1) providing encapsulated exosomes and (2) delivering the encapsulated exosomes to a target area of the body, tissue or organ.

In a seventeenth aspect, the invention provides an encapsulated exosome produced by the method including the steps of (1) collecting blood, (2) separating plasma front the collected blood, and (3) separating a solution with the exosomes therefrom, and (4) encapsulating the exosomes.

In an eighteenth aspect, the invention provides an encapsulated exosome or other vesicle, including (1) a core including platelet exosome material and (2) an encapsulant.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, claims and drawings.

DETAILED DESCRIPTION

Figure 1:
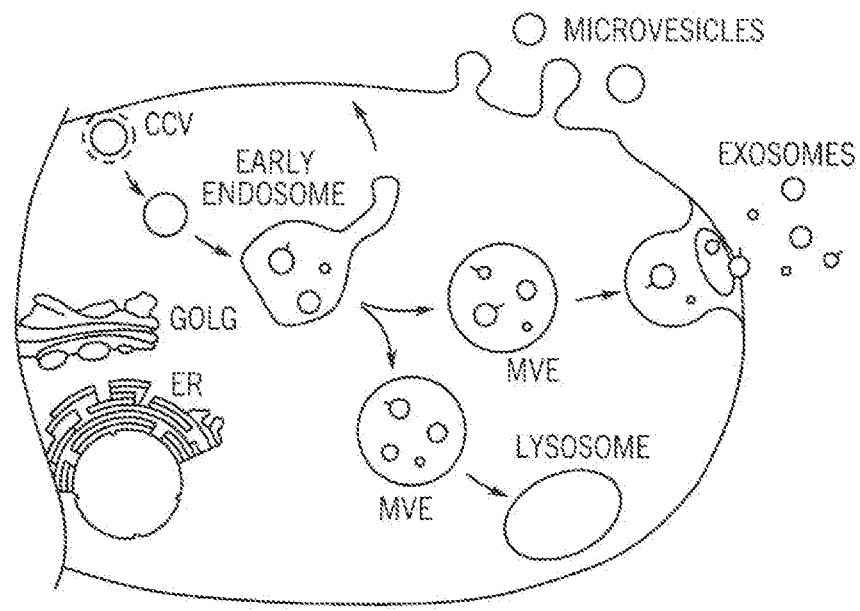
FIG. 1 illustrates a cell including, vesicles and exosomes in general.
Figure 2:
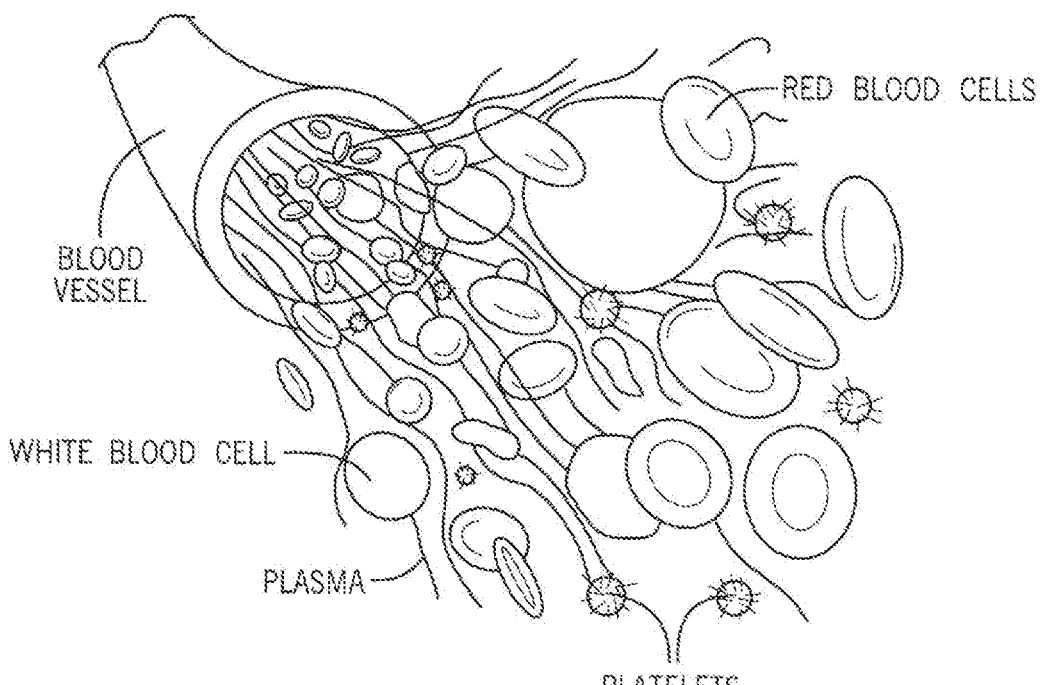
FIG. 2 illustrates the components of blood, and platelets in general.
Figure 3:
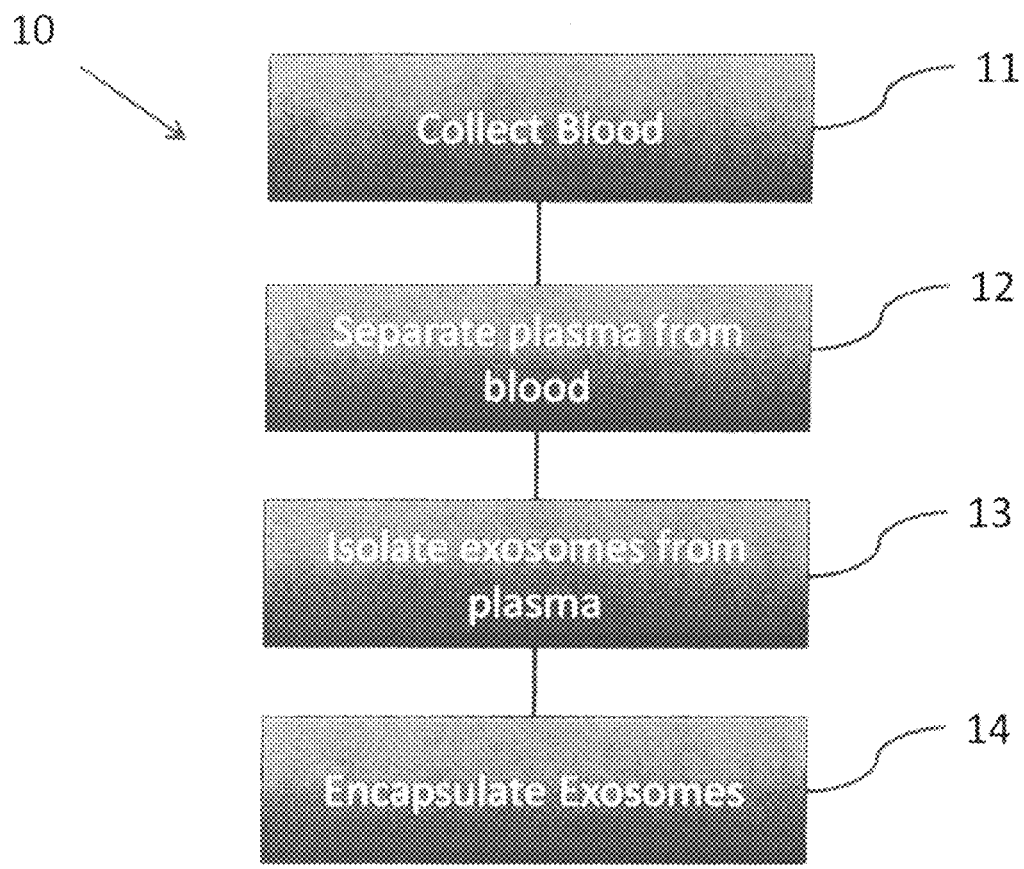
FIG. 3 is a flow chart showing a preferred embodiment of the invention of preparing encapsulated exosomes.

The present invention involves a system, apparatus, methods and compositions for gathering, purifying, encapsulating and delivering exosomes. The exosomes which are the subject of the invention are approximately 30-100 nm in diameter. The exosomes of primary interest are recovered from a platelet rich solution, following physical disruption of platelets. While there appears to be significant indication of the efficacy of exosome usage for damaged tissue regeneration, and repair, the handling and processing, and delivery of exosomes has been an unknown, heretofore An embodiment of the process of the invention involves the steps of (1) collecting blood, (2) separating plasma from the collected blood, and (3) separating the solution with the exosomes therefrom, (4) encapsulating the exosomes, and (5) delivering the exosomes. The step of collecting blood involves obtaining blood from humans or from other animals as will be described further below. The step of separating plasma may be done by several known means. The exosome fraction isolated in the third step is readily attained and concentrated through filtration, centrifugation, or other means. Where filtration is used, the material retained by the filter contains the desired exosome fraction. An exemplary filter is a 50 kDalton filter. 30 to 100 kDalton filters may be used. 50-100 kDalton filters are preferred and 50-80 kDalton filters are most preferred. Alternatively, tangential flow filtration may be used. Exemplary yields (liquid volumes) are 10-40% and 20-30%, respectively for each step. Plasma separation may yield 0.5 to 50 percent, and 3-45 percent is preferred and 10-40 percent is most preferred.

Exosome/Vesicle separation may yield 0.5 to 40 percent, and 15 to 35 percent is preferred and 20 to 30 percent is most preferred. The resultant exosome solution has the consistency of honey. In a further embodiment of the method, the exosome solution is diluted, for example by a factor of about 20, for an intended use, prior to encapsulation. Dilution may involve 100 to 1.0 percent, 25 to 2.5 percent is preferred, and 15-5 percent is most preferred. It is within the purview of the invention that plasma may be obtained from various sources. Further, processed plasma may be used, such as cryo-poor plasma.

It is believed that the exosomes and their protein payloads that are the active ingredients are sensitive to temperatures above 38° C. Therefore, a further embodiment of the process involves controlling the temperature between 40 to 150° C. at which the exosomes are maintained. The structure of the exosomes is a phospholipid bilayer structure and so the use of surfactants during processing and handling the materials of the invention is also carefully controlled. Under sterile conditions the exosomes can be stable and remain active after 6 months when stored at room temperature, so temperature is preferably controlled during storage of materials of the invention.

The process continues with the steps of (4) encapsulating the exosomes and (5) delivering the encapsulated exosomes to the desired area of the body, organ or tissue while minimizing the loss of biological activity and providing a number of desired particle size and release profiles. Again, these steps of handling and delivery of exosomes is believed to be unknown prior to this invention. To this end, the invention provides at least three (3) methods (A, B and C) for encapsulating and delivering of the starting material of the exosome concentrate, or "platelet honey," produced in step (3) preferably prior to any dilution. In each encapsulation/delivery method, different parameters such as carrier materials, exosome concentration and loading, and finally particle size of the finished material are disclosed. The final compositions produced are characterized fey methods such as active loading, scanning electron microscopy (SEM), optical microcopy, thermogravimetric (TGA) analysis, particle size distribution, specific gravity, and the like. It is within the purview of the invention that other characterization methods exist and are encompassed such as capacity to foster cell growth in vitro and pre-clinical performance over a pre-defined shelf life.

Embodiment A: Water Bead Process

The first method of encapsulating exosomes involves water, using hydrophobic fumed silica to stabilize individual droplets of aqueous solutions. This method is described in U.S. Pat. No. 6,413,548 entitled Particulate Encapsulation of Liquid Beads, assigned to AVEKA, Inc., of Woodbury, Minn. USA. This patent is hereby incorporated by reference. In general the process of making this type of bead involves the itemization of an aqueous solution into a cloud of hydrophobic fumed silica. The silica coats the liquid droplets stabilizing the droplets from coalescence when the droplets are collected. This process has been commercialized for the personal care industry for use as a hair care formulation, but its applicability to exosome encapsulation is heretofore unknown. Typically, the resultant head is 30-100 microns in diameter, 85% aqueous solution, and stable at room temperature, in a closed container for over 2 years.

Figure 4:
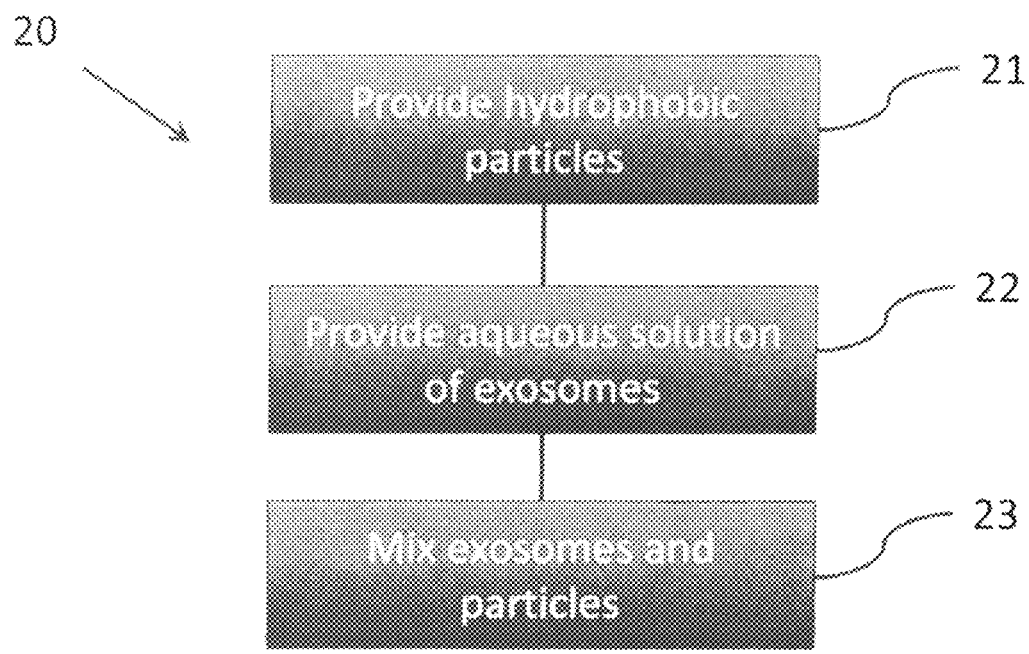
FIG. 4 is a flow chart showing an embodiment of the water bead process of encapsulation.

One particular embodiment of the sub-steps of this process of encapsulating a microvesicle involves, broadly, providing a mass of hydrophobic particles having a volume weighted mean diameter of between 0.05 and 25 micrometers, providing droplets of an aqueous exosome medium to the mass of particles, and gently mixing the fine particles of aqueous exosome medium and the hydrophobic particles to form a stable encapsulant system of droplets of the aqueous medium encapsulated by a shell of particles.

One embodiment of the resultant encapsulated micro vesicle includes a core including aqueous platelet exosomes having a predetermined percent by weight (for example at least 5 percent) water, and an encapsulant surrounding the core. The encapsulate includes at least one layer of hydrophobic particles in contact with and surrounding the core. The encapsulated microvesicle has a volume weighted mean particle diameter. An exemplary diameter is 0.05 to 25 micrometers. One geometry for the microvesicles is spherical. In one embodiment, the encapsulated microvesicle can support its own weight.

Example

Due to the expense of the platelet honey and the scarcity of the material, a relatively small sample of each formulation (~20 mL) is obtained. The platelet honey may be used as is within a therapeutic formulation. Preferably, it is diluted to enable efficient atomization, materials handling to avoid microbial contamination of the solution or final product, and sealing down of the of the process to enable production of small samples that are representative of the final process. The resultant materials are applicable for topical, including wound, applications, in tandem with potential use as biologically active biomatrix gels.

Embodiment B: Alginate Bead Process

Alginates are polysaccharide hydrocolloids that are extracted from seaweed such as the giant kelp macroystis pyrifera. The sodium conjugate base form of alginic acid is water-soluble and forms solid gels in the presence of calcium, aluminum or many other polyvalent cations.

Example

A 1-4 wt % solution of sodium alginate in water is prepared wherein the exosomes are part of the solution and dripping that alginate solution into a second solution of calcium chloride beads are immediately formed that are the shape and size of the droplet that is dripped into the calcium ion bath. By controlling the droplet size, calcium ion concentration, and time in the bath, both the particle size and the release profile of the exosomes from the particle is controlled. A number of samples with different exosome loadings and particle size distributions are produced.

Embodiment C: Spray Drying Bead Formation

Spray drying is a process wherein solutions are dried by atomizing a solution or slurry into a heated chamber. The droplets dry prior to reaching a wall. This is the most cost effective method to produce encapsulated materials, but it may have the potential to raise the temperature of the material above 38° C. Dilution and addition of adjuvants to concentrated exosomal material may allow atomization thereby providing a window to utilize this efficient approach for microencapsulation. Finally, by keeping the spray dryer outlet temperature (an indication of particle temperature) to a minimum, this approach is believed to yield enhanced exosome stability. Typically, particle size for this type of process is around 15-75 microns. Process parameters are carefully controlled, thereby permitting particle size distributions with means less than 10 microns. Moisture content can be controlled. An example is diluted platelet honey dispersed in water with a capsule or the like, via a process disclosed in U.S. Pat. No. 8,741,337.

Embodiment D: Plating Process

Plating is an encapsulation and delivery system that makes use of special materials with porosity that can take up large amounts of liquids while remaining in a powder particulate state. One advantage of this technology is it can all be done at, for example, room temperature or another controlled temperature. Such techniques are common for encapsulation and delivery of food, nutraceutical, pharmaceuticals liquids in a dry state etc., but are heretofore unknown for exosome encapsulation. In this embodiment, the process of the invention uses carrier materials such as simple sugars, modified starches, maltodextrin, porous silica, calcium carbonate etc. to optimize microencapsulation. The process may be varied to maximize loads and effectiveness. These materials, and those of the prior Examples, may be coated to effect shelf-life and/or delivery rate.

Example A

Take 2 cc of the undiluted "platelet honey" and impregnate 1 g of Huber Zeofree® 5162 silica. This can be accomplished using a FlackTek Speedmixer™ DAC 150 using 2000 rpm for 20 seconds and repeating until the undiluted "platelet honey" fully impregnates the silica. The temperature of the materials is measured and is kept below 35° C. during mixing.

Example B

Take 2 cc of the diluted "platelet honey" and impregnate 1 g of Huber Zeofree® 5162 silica. This can be accomplished using a FlackTek Speedmixer™ DAC 150 using 2000 rpm for 20 seconds and repeating until the diluted "platelet honey" fully impregnates the silica. The temperature of the materials is measured and is kept below 35° C. during mixing.

The invention also provides a process of commercially separating platelet exosomes. Exosomes of the invention may be collected from human blood. Similar results are believed to be obtainable from, porcine (pig) or bovine (cow) plasma which has been collected and separated for appropriate exosomes. Although the process of extraction is similar, access to large quantities of blood from these sources provides scalability that may not be readily achievable with human plasma.

Referring to FIG. 3, in summary, shows an embodiment of the method 10 of forming encapsulated exosomes of the invention. Firstly, blood is collected 11. Next, plasma is separated 12 from the blood. The liquid volume yield is approximately 10-40 percent. Then, exosomes are separated 13 from the plasma, preferably by physical disruption of the platelets and then via a filter, most preferably a 50 kDalton filter. The liquid volume yield is approximately 20-30 percent in this step. Exosomes isolated are approximately 30-100 nm size. Next, the exosomes are encapsulated 14. Encapsulation 14 may be accomplished by the water bead process 20 shown in the flow chart of FIG. 4. This involves providing 21 hydrophobic particles of a predetermined profile, A solution of exosomes are also provided 22. Finally, the exosomes and particles are mixed 23.

Figure 5:
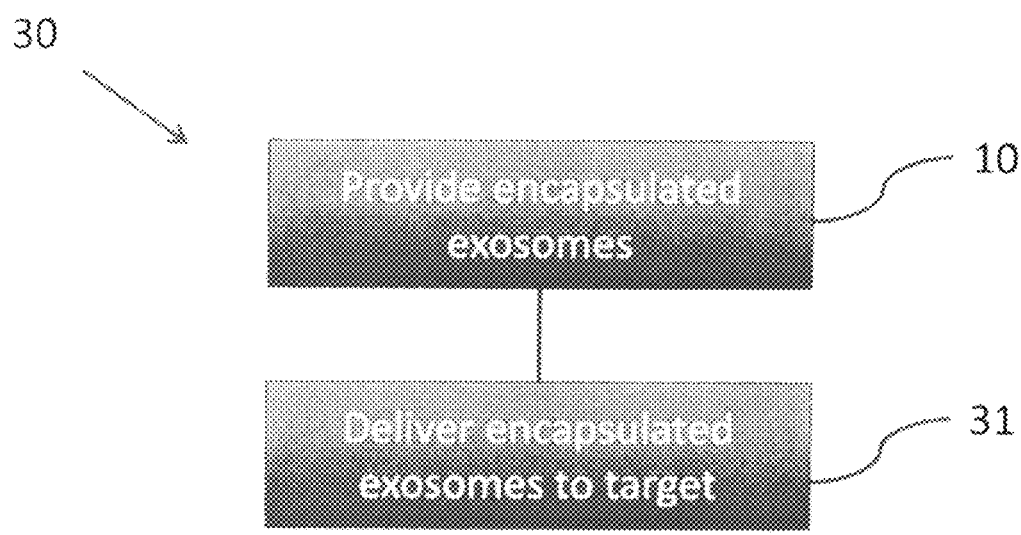
FIG. 5 is a flow chart showing a preferred embodiment of the method of delivering encapsulated exosomes to a biological target.

FIG. 5 shows a process of delivering encapsulated exosomes to a target for therapeutic or other purposes. Firstly, encapsulated exosomes are provided 10 by the process shown in FIG. 1, and described above. Next, the encapsulated exosomes 10 are delivered 31 to the target.

This technology is believed to be useful for clinical, cosmetic and veterinary applications. Specifically these materials are useful for topical applications in the cosmetic field, wound dressing applications for animal/pet and human applications, and the direct injection into damaged heart or other tissue. Furthermore, purified nanovesicle/exosomal fraction is useable as pat of a biomatrix gel for fibromuscular, osteogenic, chondrogenic, adipogenic or other regeneration. Thus, the technology platform may be complexed with biodegradable meshes for colorectal/gynecological surgeries (fistulas, non-healing erosions, pelvic organ prolapse), ENT procedures (osteoradionecrosis), plastic surgery/wound healing (limitation of scar, rapid healing, non-healing wounds), orthopedic procedure (non-union, avascular necrosis). Each one of these applications presents different delivery concerns. Similarly, wound applications and direct injection applications require sustained slow delivery over days to up to 6 months.

Figure 8:
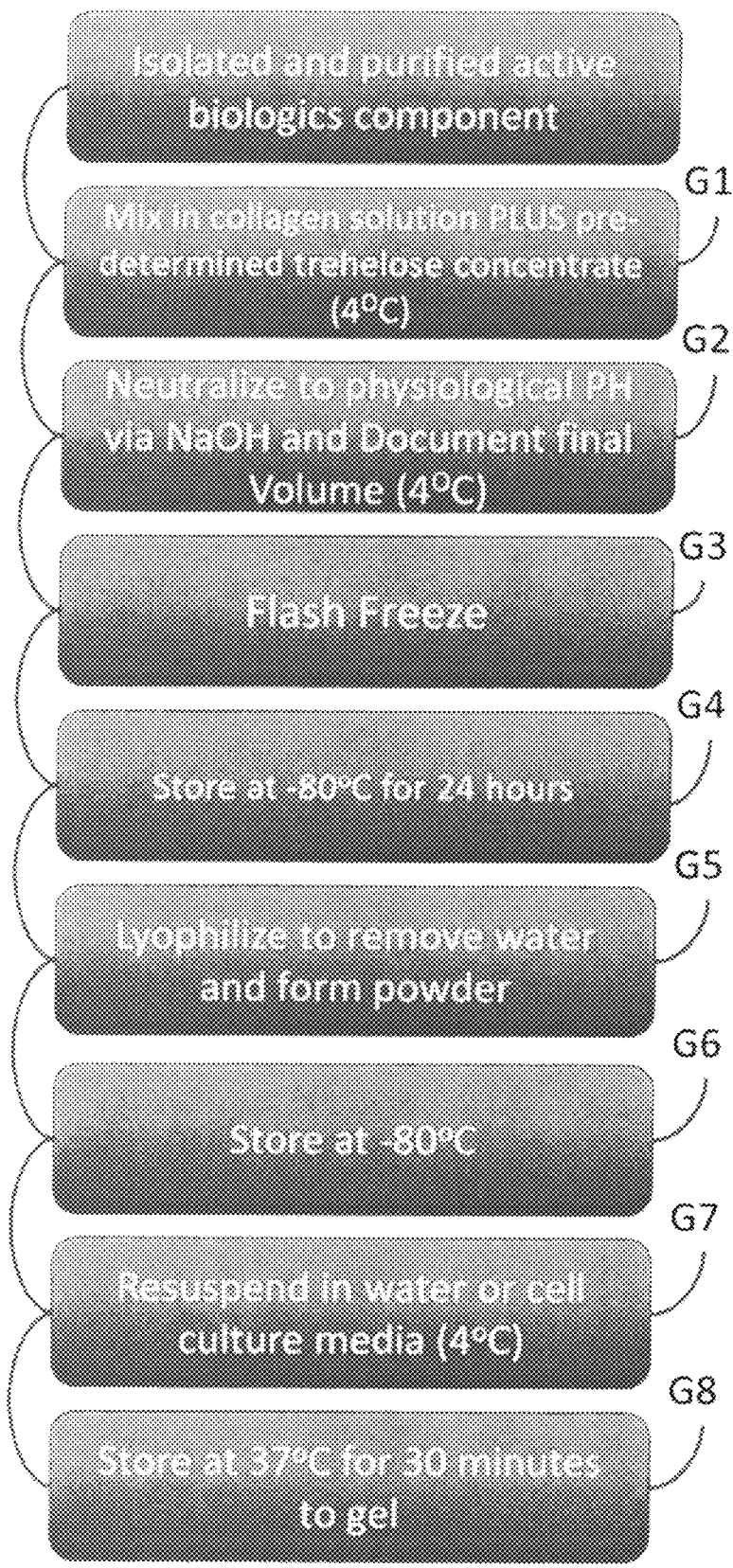
FIG. 8 is a flowchart for a preferred embodiment of the method of forming a bio-matrix gel.

Referring to FIG. 8, the invention further provides a method of preparing a biomatrix gel. One embodiment of the method is as follows.

1. Following isolation of the platelet component (via exosome and/or about 30-30 KD cutoff) this component is mixed in a collagenous solution along with the trehalose concentration range established in the protocol described below.
2. This solution is then neutralized to physiological pH via de addition of NaOH. A final volume is documented.
3. The Solution is immediately flash frozen in liquid nitrogen until it is completely frozen
4. The solution is immediately stored in −80 for at least 24 hours
5. This was then lyophilized until all water was removed. A powder material is formed.
6. The powder can be stored at −80 C
7. The powder can be resuspended in water or cell culture media by addition of the volume documented in Step 2.
8. This material is then stored at 37 C for gelling.
9. After 30 minutes the product is completely gelled.

Preferably, each of the above steps is performed with samples in ice to prevent premature gelling.

Figure 6:
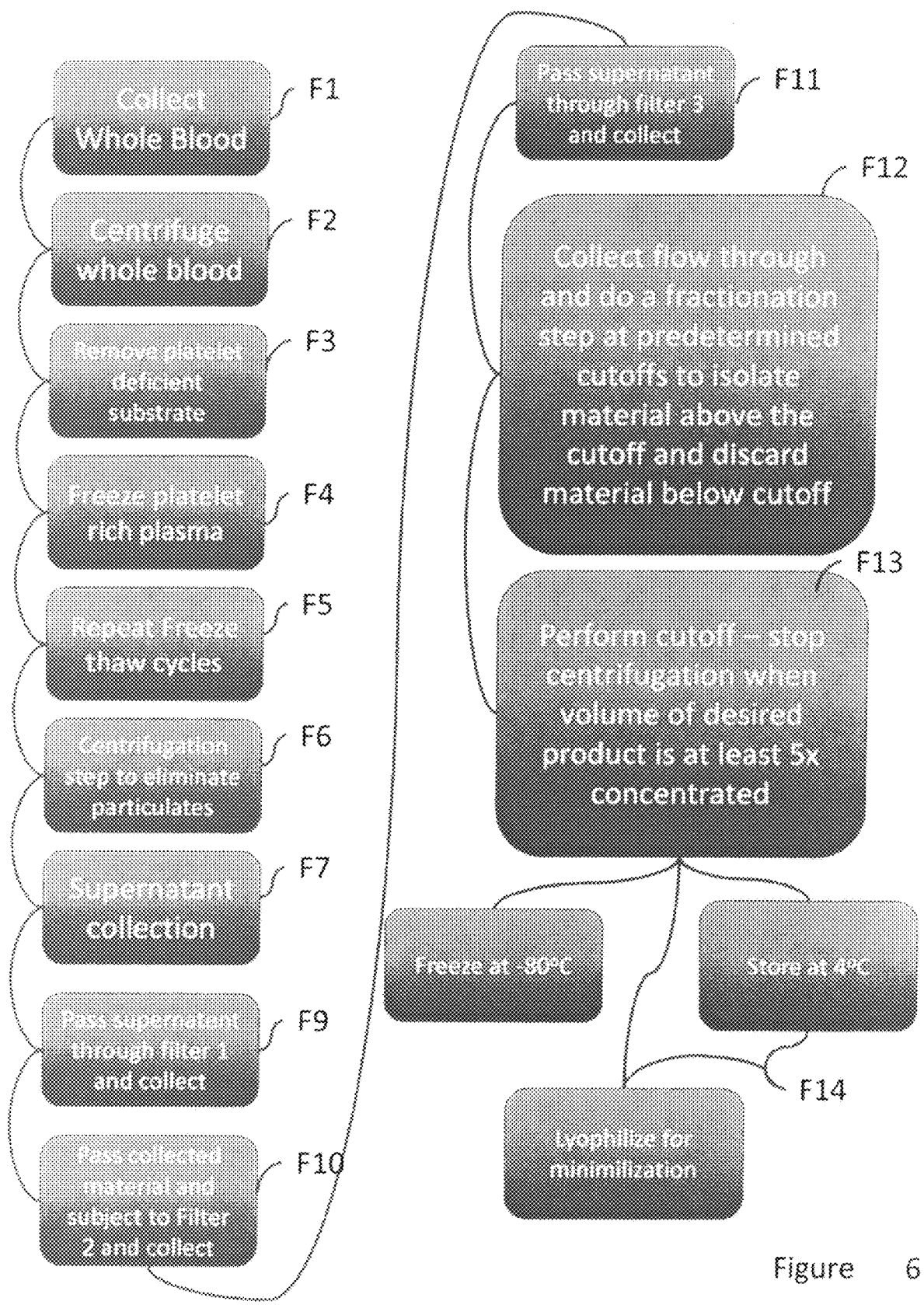
FIG. 6 is a flowchart for a preferred embodiment of the method of fractionating platelets.

Referring to FIG. 6, the invention further provides a method of fractionating platelets. One embodiment of the method includes the steps of:

1. collect whole blood
2. centrifuge whole blood for at least 1500 rpm for at least 15 minutes (alternatively whole blood, can be stored at 4 C to allow RBC to precipitate for at least 4 hours)
3. remove platelet poor plasma (around ⅔ of supernatant) and isolate remaining ⅓ of supernatant)
4. flash freeze platelet rich plasma in liquid nitrogen and store in −80 c for at least 24 hours
5. allow platelet rich plasma to thaw in water bath in a temperature between 25 c and 37 c, and preferably repeat freeze-thaw cycles
6. Centrifuge thawed PL at 500 g for 10 minutes
7. Collect supernatant and discard pellet
8. Intentionally Left Blank
9. Pass supernatant through 70 um filter and collect
10. Pass collection of prior step through a 40 um filter
11. Filter collection of prior step through a 0.2 um filter
12. Collect the flow through and do platelet fractionation via a 30 or 50 kD cutoff. Here we are isolating whatever is above these values and what's below is discarded.
13. Perform 30 or 50 kd cutoff via centrifugation. In this step the settings of the centrifuge vary depending on filter. Stop centrifugation when the volume of the desired product is at least 5× less than the initial input volume.
14. The isolate will have a viscous honey like consistency which can be (a) directly frozen at −80 c for long term storage, (b) stored at 4 c for use or (c) lyophilized for micronization.

Figure 7:
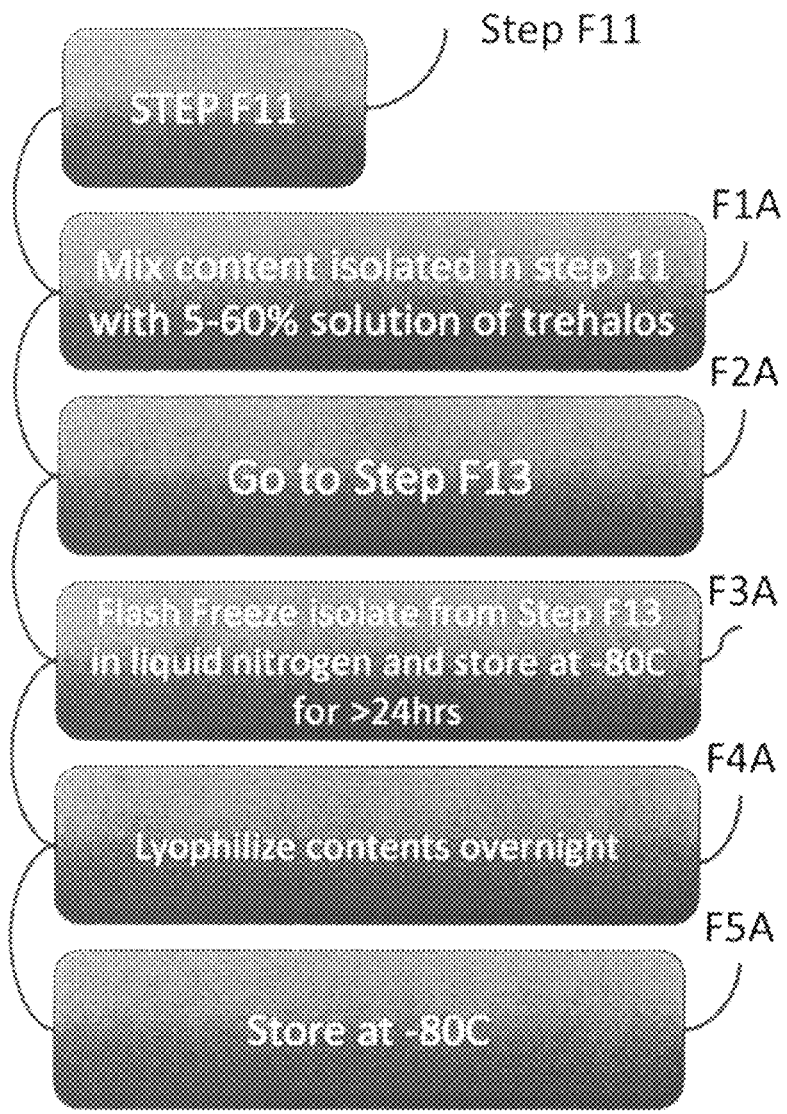
FIG. 7 is a flow chart for a preferred embodiment of the method of lyophilizing platelets.

Referring to FIG. 7, the invention still further provides a method of lyophilizing platelets. One embodiment of the method includes the steps of:

1. Before Step 12 (above), mix the contents of step 13 with a 5-60% solution of trehalos,
2. Continue to Step 13 above,
3. Flash freeze the isolate from Step 13 in liquid Nitrogen and Store at −80 C for at least 24 hours,
4. Lyophilize contents overnight, and
5. Store lyophilized material at −80 C.

Although the system, composition, and methods herein have been described in connection with exosomes, it is within the purview of the invention that the technology may be applied to other vesicles.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A method of preparing microvesicles comprising the steps of:
   providing blood;
   separating plasma from the provided blood, thereby providing platelet-rich plasma;
   subjecting the platelet-rich plasma to at least two cycles of:
      freezing the platelet-rich plasma; and
      thawing the frozen platelet-rich plasma; and separating a solution with the microvesicles from the thawed platelet-rich plasma.

2. The method of claim 1, wherein the provided blood is collected from humans, pigs or cows.

3. The method of claim 1, wherein the liquid volume of plasma separated from the blood is 10-40 percent.

4. The method of claim 1, wherein the microvesicles are exosomes.

5. The method of claim 4, wherein the step of separating a solution of exosomes from the separated plasma is accomplished via filtration, whereby the solution of exosomes is retained by the filter.

6. The method of claim 5, wherein filtration is accomplished with a 30 to 100 kDalton filter.

7. The method of claim 6, wherein the filter is a 50 to 80 kDalton filter.

8. The method of claim 4, wherein the step of separating a solution of exosomes from the thawed platelet-rich plasma is accomplished via centrifugation.

9. The method of claim 1, wherein the liquid volume of microvesicles extracted from the plasma is 0.5 to 40 percent.

10. The method of claim 9, wherein the liquid volume of microvesicles extracted from the plasma is 20-30 percent.

11. The method of claim 1, wherein the microvesicle solution derived is diluted 100 to 1.0 percent.

12. The method of claim 11, wherein the microvesicle solution is diluted 15 to 5 percent.

13. The method of claim 1, further comprising the step of combining the microvesicles with a base material.

14. The method of claim 13, wherein the base material is a biomatrix gel.

15. The method of claim 14, wherein the combination of microvesicles and base material is coated with a predetermined material.

16. The method of claim 1, further comprising the steps of controlling the temperature at which the abovementioned steps are accomplished.

17. The method of claim 1, wherein:
the liquid volume of plasma separated from the blood is 10-40 percent;
the microvesicles are exosomes;
the step of separating a solution of exosomes from the separated plasma is accomplished via filtration or centrifugation;
the liquid volume of exosomes extracted from the plasma is 0.5 to 40 percent; and
the exosome solution is diluted 15 to 5 percent.

18. The method of claim 1, further comprising encapsulating the microvesicles.

19. The method of claim 17, wherein the step of encapsulating the exosomes is accomplished by water bead delivery, alginate bead delivery, spray drying bead formation, or plating delivery.

20. The method of claim 18, wherein the step of encapsulating microvesicles is accomplished by water bead delivery.

21. The method of claim 18, wherein the step of encapsulating microvesicles is accomplished by alginate bead delivery.

22. The method of claim 18, wherein the step of encapsulating microvesicles is accomplished by spray drying bead formation.

23. The method of claim 18, wherein the step of encapsulating microvesicles is accomplished by plating delivery.

24. A composition comprising:
microvesicles prepared according to the method of claim 1; and
a carrier.

25. The composition of claim 24, wherein the microvesicles comprises a core, including platelet exosome material, and an encapsulant.

26. The composition of claim 25, wherein the encapsulant is at least one layer of hydrophobic particles in contact with and surrounding the core.

27. The composition of claim 24 wherein:
the microvesicles comprise a core, including platelet exosome material, and an encapsulant;
the microvesicles are separated from plasma;
the encapsulant is at least one layer of hydrophobic particles in contact with and surrounding the core, formed by water bead delivery, alginate bead delivery, spray drying bead formation or plating delivery, and
the carrier is a biomatrix gel.

* * * * *